United States Patent [19]
Bryan

[11] Patent Number: 5,723,773
[45] Date of Patent: Mar. 3, 1998

[54] BUBBLE DETECTOR

[75] Inventor: Michael Bryan, Watford, United Kingdom

[73] Assignee: Eastman Kodak Company, Rochester, N.Y.

[21] Appl. No.: 753,307

[22] Filed: Nov. 22, 1996

[30] Foreign Application Priority Data

Dec. 6, 1995 [GB] United Kingdom ............... 9524949

[51] Int. Cl.$^6$ ............... G01N 29/02; G01N 15/06
[52] U.S. Cl. ............... 73/61.75; 73/54.15; 73/589; 73/629; 73/19.1; 324/725; 310/338; 310/323; 310/334
[58] Field of Search ............... 73/61.75, 61.49, 73/54.15, 61.79, 589, 629, 19.1, 19.08, 19.06, 19.03; 324/725

[56] References Cited

U.S. PATENT DOCUMENTS

| | | | |
|---|---|---|---|
| 3,774,717 | 11/1973 | Chodorow | 181/0.5 NP |
| 3,921,622 | 11/1975 | Cole | 128/2 V |
| 3,974,681 | 8/1976 | Namery | 73/67.5 R |
| 4,278,932 | 7/1981 | Tait | 324/57 R |
| 4,319,580 | 3/1982 | Colley et al. | 128/661 |
| 4,325,255 | 4/1982 | Howard et al. | 73/589 |
| 4,339,247 | 7/1982 | Faulkner et al. | 55/12 |
| 4,384,476 | 5/1983 | Black et al. | 73/61 R |
| 4,478,072 | 10/1984 | Brown | 73/61 R |
| 4,563,895 | 1/1986 | Eckert | 73/61 R |
| 4,607,520 | 8/1986 | Dam | 73/19 |
| 4,731,556 | 3/1988 | Adams | 310/338 |
| 5,394,732 | 3/1995 | Johnson et al. | 73/19.1 |

FOREIGN PATENT DOCUMENTS

| | | |
|---|---|---|
| 0 053 453 A | 6/1982 | European Pat. Off. . |
| 0 524 605 A1 | 1/1993 | European Pat. Off. . |
| 0 643 301 A1 | 3/1995 | European Pat. Off. . |
| 1091035 | 7/1989 | Japan . |
| 91 16087 A | 10/1991 | WIPO . |
| 96 21151 A | 7/1996 | WIPO . |

*Primary Examiner*—Hezron E. Williams
*Assistant Examiner*—J. David Wiggins
*Attorney, Agent, or Firm*—Mark G. Bocchetti

[57] ABSTRACT

The presence of bubbles on such photographic material, as is well known, results in significant defects in the photographic materials produced so that it is important, in the manufacture of such photographic materials, to detect the presence of such bubbles in the liquid emulsion and to take appropriate remedial action. Described herein is a bubble detector comprising a conduit for liquid to be monitored, the conduit having opposing flattened, generally parallel walls, and a transducer engaged with one of the generally parallel walls and operable to apply alternating displacements to one of the generally parallel walls, at an ultrasonic frequency, in a direction generally normal to the generally parallel walls to transmit sonic or ultrasonic waves through liquid passing through the conduit.

16 Claims, 7 Drawing Sheets

FIG. 10

BUBBLE DETECTOR

FIELD OF THE INVENTION

The present invention relates to apparatus for detecting bubbles in a liquid flowing through a conduit and more particularly to such apparatus in which bubble detection is carried out sonically or ultrasonically. The invention is particularly, but not exclusively, applicable to the detection of bubbles in liquid photographic emulsion flowing to coating apparatus for coating film and paper for photography.

BACKGROUND OF THE INVENTION

The presence of bubbles on such photographic material, as is well known, results in significant defects in the photographic materials produced so that it is important, in the manufacture of such photographic materials, to detect the presence of such bubbles in the liquid emulsion and to take appropriate remedial action.

Various forms of bubble detector for this purpose have been proposed, including detectors using ultrasound. In particular, ultrasonic detectors using the method of attenuation of ultrasound have been utilized in photographic emulsion delivery systems. Ideally, in photographic emulsion coating systems, no bubbles at all should be present in the emulsion coated onto film, paper, etc. and certainly no bubbles must be present of a size to produce a detectable defect in the finished product.

The appearance of bubbles in the coating stage and immediately preceding that stage generally indicates that some part of the system upstream of that stage has become defective, for example that a valve or seal has become faulty, allowing air to pass into the system.

However, known bubble detectors for photographic emulsion delivery systems do not afford reliable detection of bubbles. The detectors used hitherto, utilizing ultrasound attenuation methods are on the one hand also sensitive to solids and turbulence in the liquid and on the other hand also have "dead" spots in the sampling volume and so may fail to detect bubbles.

As the remedial action required in a photographic emulsion delivery and coating system, in the event that bubbles are believed to be present, is of a relatively drastic nature, involving the shut-down of the respective coating track, the loss of substantial quantities of emulsion and stock, and manual inspection of the system involving dismantling and re-assembling part of the system with subsequent purging and testing before normal production is resumed, spurious bubble detection incurs a heavy penalty in production costs. Conversely, failure to detect the occurrence of bubbles promptly may result in defective photographic materials being passed for distribution and sale, with serious consequences in the market.

SUMMARY OF THE INVENTION

There is, accordingly, a pressing demand for a bubble detector which can be used in photographic emulsion delivery systems, which is not prone to signal the presence of bubbles when bubbles are not present and which will afford reliable detection of bubbles when these are present.

It is one object of the present invention to provide an improved ultrasonic bubble detector meeting these requirements.

According to one aspect of the present invention, there is provided a sonic or ultrasonic bubble detector comprising a sonic or ultrasonic transducer placed in sound or ultrasound transmitting relationship with a conduit for fluid flow, means for supplying an a.c. electrical signal to said transducer to cause the transducer to generate and to direct across or through said conduit corresponding sonic or ultrasonic energy, and means for sensing the impedance of said transducer to said electrical signal and for detecting from variations in said impedance the presence of bubbles in the liquid flowing through said conduit.

According to another aspect of the present invention, there is provided a bubble detector comprising a conduit for liquid to be monitored, said conduit having opposing flattened, generally parallel walls, and a transducer engaged with one of said walls and operable to apply alternating displacements to said one of said walls, in a direction generally normal to said walls to transmit sonic or ultrasonic waves through liquid passing through said conduit.

While, in accordance with this aspect of the invention, it would be possible to use two transducers disposed opposite one another, engaged with respective ones of said opposing side walls, one transducer acting as a transmitter and the other acting as a receiver, or, indeed, to use two transducers engaged with said conduit at locations spaced apart therealong, one said transducer acting as a transmitter and the other as a receiver, it is preferred to use a single transducer acting, in effect, as transmitter and receiver, in accordance with the first-noted aspect of the invention, and thereby avoid the need for matching one transducer with another which would normally arise using separate transmitter and receiver transducers.

According to a yet further aspect of the invention, there is provided a bubble detector comprising means for generating a sonic or ultrasonic signal with a frequency of 100 kHz or lower.

The applicants have found that the use of a frequency of the order of 50 kHz in detection of bubbles in photographic emulsion coating systems, rather than the significantly higher frequencies used in prior ultrasonic bubble detectors, allows detection of bubbles which are large enough to present a problem in emulsion coating systems namely bubbles of 60 μm and larger whilst permitting excellent discrimination between bubbles and solid particles. Ultrasonic bubble detectors utilizing significantly higher frequencies have been found to be sensitive to solid particles in the emulsion. Whilst solid particles of significant size in a photographic emulsion are also undesirable, the possible causes of and remedies for the presence of such solid particles are quite different from the causes of and remedies for the presence of bubbles, so that a response of a detector to a solid particle as if it were a bubble is unhelpful. The lower frequency limit for the ultrasonic signal used is determined by the consideration that the frequency used may not be lower than the resonant frequency of the smallest bubble to be detected which has been found to be approximately 50 kHz for a bubble 60 μm in diameter.

The invention may find application in fields other than photographic coating. For example, it is envisaged that the bubble detector of the present invention may be of utility in blood transfusion and like equipment.

Likewise, air bubbles, or at any rate bubbles of non-sterile air, are undesirable in food products or confectionery, so that the bubble detector of the present invention may also be useful in food processing systems or confectionery manufacturing equipment.

It will be appreciated that in such other fields of application of the invention, the sizes of the bubbles which are of interest and/or the sizes of the solid particles which may be present in the medium detected, may render advantageous a frequency lower or higher than the 50 kHz frequency which the applicants have found ideal for bubble detection in photographic emulsion.

BRIEF DESCRIPTION OF THE DRAWINGS

For a better understanding of the present invention, reference will now be made, by way of example only, to the accompanying drawings in which.

DETAILED DESCRIPTION OF THE INVENTION

Referring to the drawings, the apparatus includes a sensor pipe 10 in the form of a length of metal tubing of circular section over most of its length but flattened over a middle section to afford two parallel flat wall portions. The extent to which the metal tube is thus flattened is selected to afford such flat wall portion of adequate width without substantially reducing the flow cross-section of the tube in the region between said flat wall portions and thus without substantially altering flow conditions through the pipe. An ultrasonic transducer head 16 is secured to one of the flat walls in the central section of pipe 10 and projects substantially perpendicularly from the pipe 10 relative to the longitudinal axis of the pipe. Ultrasound-absorbing lengths 18 of rubber tubing are fitted tightly over the pipe 10 and extend to the transducer head.

In one example of the invention, the sensor pipe 10 has a diameter of 15 mm adjacent its ends and is flattened in its middle region to afford a gap of around 6 mm between the flat wall portions.

As explained below, the ultrasonic head has an operating frequency around 50 kHz. The pipe 10 is dimensioned so as to be tuned to the same frequency. In the apparatus of FIGS. 1 to 4, the free ends of the pipe 10 stop short of the free ends of pipe stubs 11 which pass through and are secured to respective opposite end walls of a housing 13 of the apparatus, the pipe stubs 11 being co-axial with the sensor pipe 10.

Each length 18 of rubber tubing extends past the respective end of the sensor pipe and over the adjacent end of the adjacent pipe stub 11 and thus also provides a connection for fluid flow between the pipe 10 and the respective stub 11. Clips 15 on each length 18 of rubber tubing clamp the tubing to the respective pipe stub 11 and to the adjoining end of the sensor pipe. In use of the apparatus the apparatus is connected in a pipeline for conveying the liquid to be monitored, namely liquid photographic emulsion in the example described, respective pans of the pipeline upstream and downstream of the apparatus being connected to respective ones of the stubs 11. Alternatively, reinforced rubber piping may be, used for lengths 18 and clips 15 dispensed with. The rubber tubing serves to provide a fluid tight connection between the stubs 11 and pipe 10 and at the same time serves to dampen the vibrations of the pipe 10 and to isolate the pipe 10 from stubs 11 as regards ultrasonic vibration. The rubber tubing also isolates the pipe 10 and transducer from mechanical vibrations transmitted to the apparatus via the pipeline in which it is connected. The rubber tubing also serves the significant purpose, as explained below, of lowering the working Q of the system.

The transducer head consists of a "Langevin sandwich" type transducer bolted to an ultrasound-conducting and directing element 20 referred to herein for convenience as a "horn" and which comprises a tapering metal bar or rod secured at its narrower end to pipe 10. The transducer head is resonant at a frequency of 50 kHz. The horn 20 and sensor pipe 10 are designed and adjusted to be resonant at the same frequency of 50 kHz. The transducer head is relatively insensitive to mechanical vibration but is preferably mounted on rubber couplings for isolation from externally originating vibrations.

Considering the construction of the transducer and horn assembly in greater detail, the horn 20 has a screw-threaded bore extending longitudinally from the end face at its broader end, which bore receives a screw-threaded bolt 24. The bolt 24 passes through a stack of annular components comprising, in order from the horn, an aluminum gasket 17, a first annular metal end mass 26, a first annular piezo electric crystal 28, a first annular washer and contact plate 30 mounted so as to be insulated from the bolt and having a radially extending contact tag, a second annular piezo-electric crystal 32, a second annular washer and contact plate 34 having a radially extending contact tag, and a second annular metal end mass 36. The end masses 26 and 36 are of equal diameter whilst the crystals 28 and 32 are of a diameter slightly smaller than the end masses 26 and 36. The diameter of the horn at its wider end adjoining the transducer is equal to that of each of said annular components. The crystals 28 and 30 are matched, in manner known per se, as are the end masses 26 and 36. The bolt 24 effectively forms part of the tuned element constituted by the horn 20 and is taken into account in designing and adjusting the resonant frequency of the horn. The second annular end mass 36 has a smooth internal bore receiving the bolt 24, whereas the first annular end mass 36 has an internally screwthreaded bore which screwthreadedly engages the screw-threaded part of the bolt shank. The end mass 26 thus also acts as a nut screwed onto the bolt and the crystals 28 and 32, washers 30 and 34 and end mass 36 are clamped tightly between the bolt head and the end mass 26. The bolt 24, thus carrying the transducer comprises crystals 28 and 32 and the end masses 26 and 36 is, in assembly, screwed into the horn 20 until the end mass 26 abuts the end face of the horn, but need not be screwed very tightly against the horn, the torque required to screw the transducer into the horn being substantially smaller than that required to screw the end mass 26 onto the bolt to clamp the end mass 36 and 15 crystals 28 and 32. This feature makes it possible, when necessary, to unscrew the transducer from the horn, for replacement, and to screw the replacement onto the horn; without special tools and without the risk of damage to the sensor pipes or the connection of the horn with the sensor pipe.

It has been found that the dimensions of the crystals used, should be such as to give a first."crystal only" resonance at least 50% higher than the desired final working frequency of the transducer. In use, the transducer is driven by a 50 kHz a.c. signal, applied between contact plates 30 and 34 by driving circuitry described below.

The length of said assembly of annular elements, forming the Langevin sandwich, is preferably at least 50% longer than its diameter. The final assembly is coated with polyurethane varnish to keep out moisture.

The tip of the horn is silver soldered onto one flat wall of the sensor pipe 10, which acts rather like a matched load on the transducer.

As noted above, the horn and the sensor pipe 10 are separately tuned to the resonant frequency of the transducer.

The rubber tubing 18 is selected so as to reduce the working electrical Q factor of the transducer head to about 25 (high damping regime). With a working Q factor of 25 the driving circuitry driving the transducer can be very simple, as minor frequency drift is then of no great importance. Sensitivity of the head is lost of course by lowering the Q in this way, but the transducer is so efficient in the first place that when used at a Q of 25 it still provides a very good S/N ratio for detection of small bubbles. Furthermore, the lowering of the Q in this way renders negligible in effect the fairly substantial variations in Q which may occur, between different nominally identical transducer/horn/sensor pipe assemblies, thereby making practicable volume production of the bubble detector without provision for or need for involved tuning procedures on set-up or in use of the apparatus.

It will be appreciated that with the exemplified dimensions Of sensor pipe 10, the maximum cross-sectional dimension of the pipe 10 is substantially less than one wavelength, in the liquid emulsion, of the 50 kHz ultrasound used. Consequently transverse standing waves are not Set up and there are no "dead" zones through which an otherwise detectable bubble can pass to avoid detection.

The flattening of the sensor pipe 10 in the region to which the horn 20 is secured, besides facilitating the mounting of the horn, causes the wall of the pipe to which the horn 20 is attached to act rather like a diaphragm, ensuring that a significant proportion of the ultrasonic energy transmitted by the horn 20 is transmitted through the liquid within the pipe rather than, for example, being largely confined to the metal of the sensor pipe. As noted above, the extent of such flattening is kept below that which would substantially reduce the flow cross-section of the pipe and accordingly, fluid flow through the sensor pipe is hardly impeded by the flattening.

The electrical impedance of the transducer is dependent, inter alia, upon the mechanical impedance of the system including the fluid filled sensor pipe 10 which in turn varies according to whether or not bubbles are present in such fluid in the region of the tip of the horn 20 and upon the size and/or number of such bubbles, if present. The detector circuitry associated with the transducer serves to detect changes in the electrical impedance of the transducer and to provide signals representative of such changes to a chart recorder or other display device.

Figure 1:
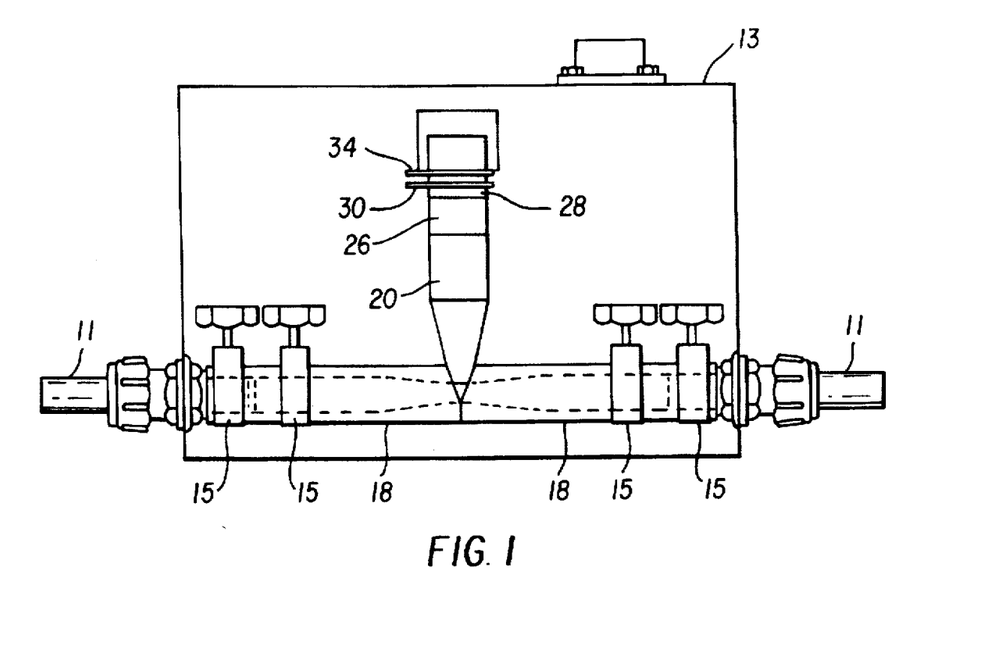
FIG. 1 is a side elevation view of part of a bubble detector in accordance with the invention, with a casing thereof shown in phantom.
Figure 2:
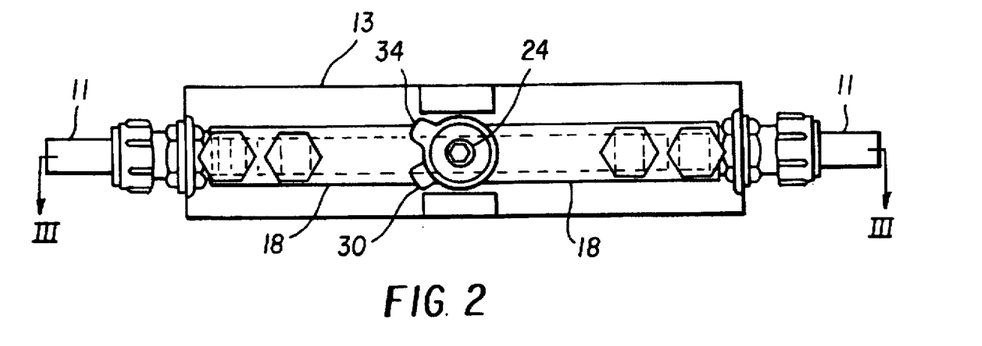
FIG. 2 is a plan view of the apparatus shown in FIG. 1, with the casing again shown in phantom.
Figure 3:
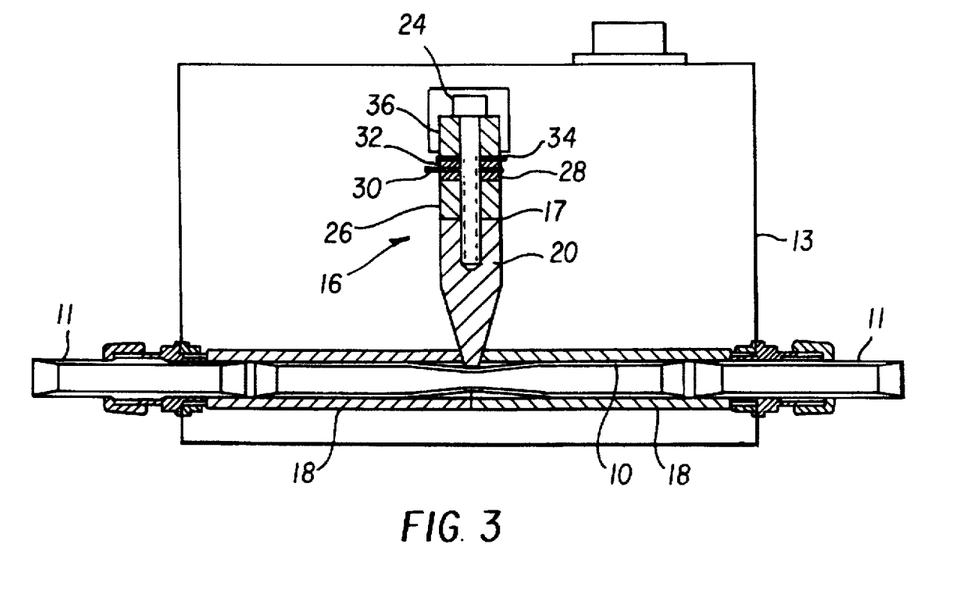
FIG. 3 is a view in section taken along the line III—III in FIG. 2, i.e. along the axis of the sensor pipe.
Figure 4:
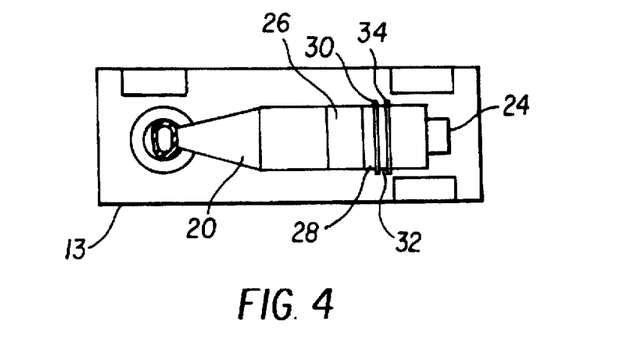
FIG. 4 is a view of the apparatus shown in FIGS. 1 to 3 in end elevation, with parts omitted for clarity.
Figure 5:
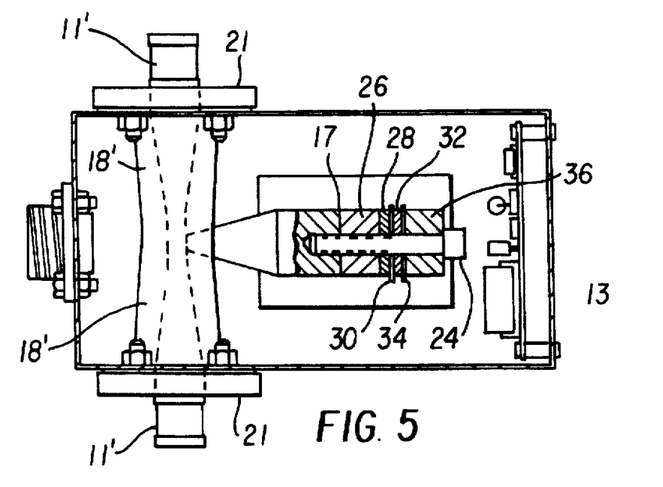
FIG. 5 is a view corresponding to FIG. 1, (but turned on one end) of a variant of the apparatus shown in FIG. 1.
Figure 6:
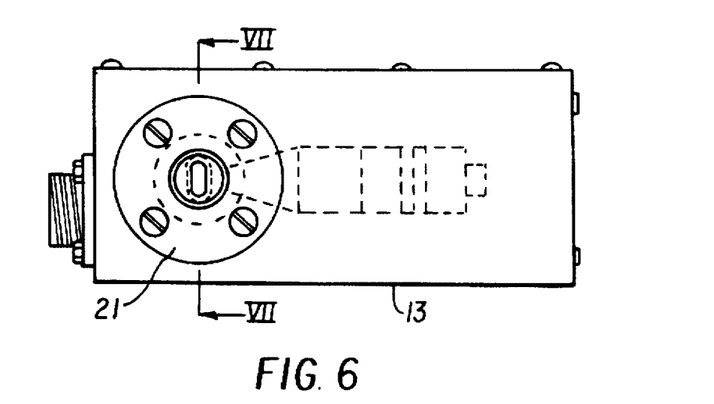
FIG. 6 is an end elevation view corresponding to FIG. 5.
Figure 7:
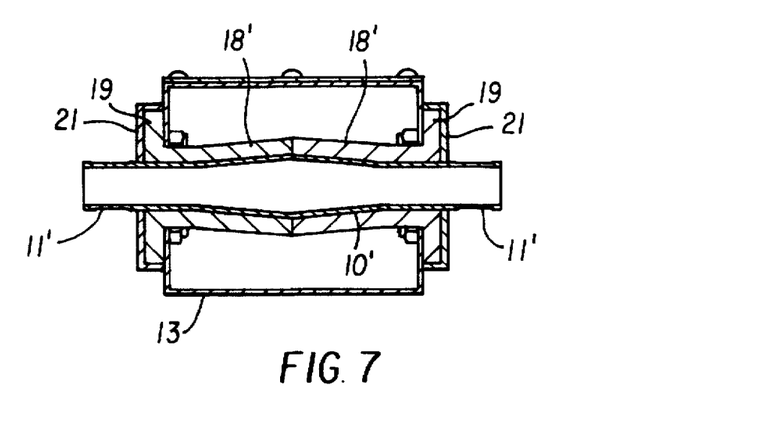
FIG. 7 is a view in section along the line VII—VII in FIG. 6, along the axis of the sensor pipe.

The variant shown in FIGS. 5, 6 and 7 differs from that of FIGS. 1 to 4 principally in that the sensor pipe 10' and the pipe stops 11' are integral with one another, that is to say, the sensor pipe 10' projects through opposing sides of the housing, with the ends of the sensor pipe 10' providing pipe stops 11' for connection, via appropriate unions (not shown), with upstream and downstream portions of the emulsion pipeline. In this variant, the lengths of rubber tubing are replaced by purpose-made rubber sleeves 18', each having at its end remote from the transducer horn, an annular flange 19. In this variant, the sleeves 18' are extended, over the respective ends of the sensor pipe, through apertures in opposing side walls of the housing, from the outside and are clamped between the respective said side wall and a respective annular washer 21. The construction of the transducer assembly is shown more clearly in FIG. 5 than in FIG. 3.

The variant of FIGS. 5 to 7, whilst it is marginally more sensitive than that of FIGS. 1 to 4 to vibrations from the pipeline in which it is connected is, in practice, still adequately insensitive to such vibrations from the sonic or ultrasound source as are likely to be encountered in practice and provides a higher assurance of integrity of sealing against leaks within the housing as might occur, for example, after prolonged use of the variant of FIGS. 1 to 4 through aging of the rubber piping.

Figure 8:
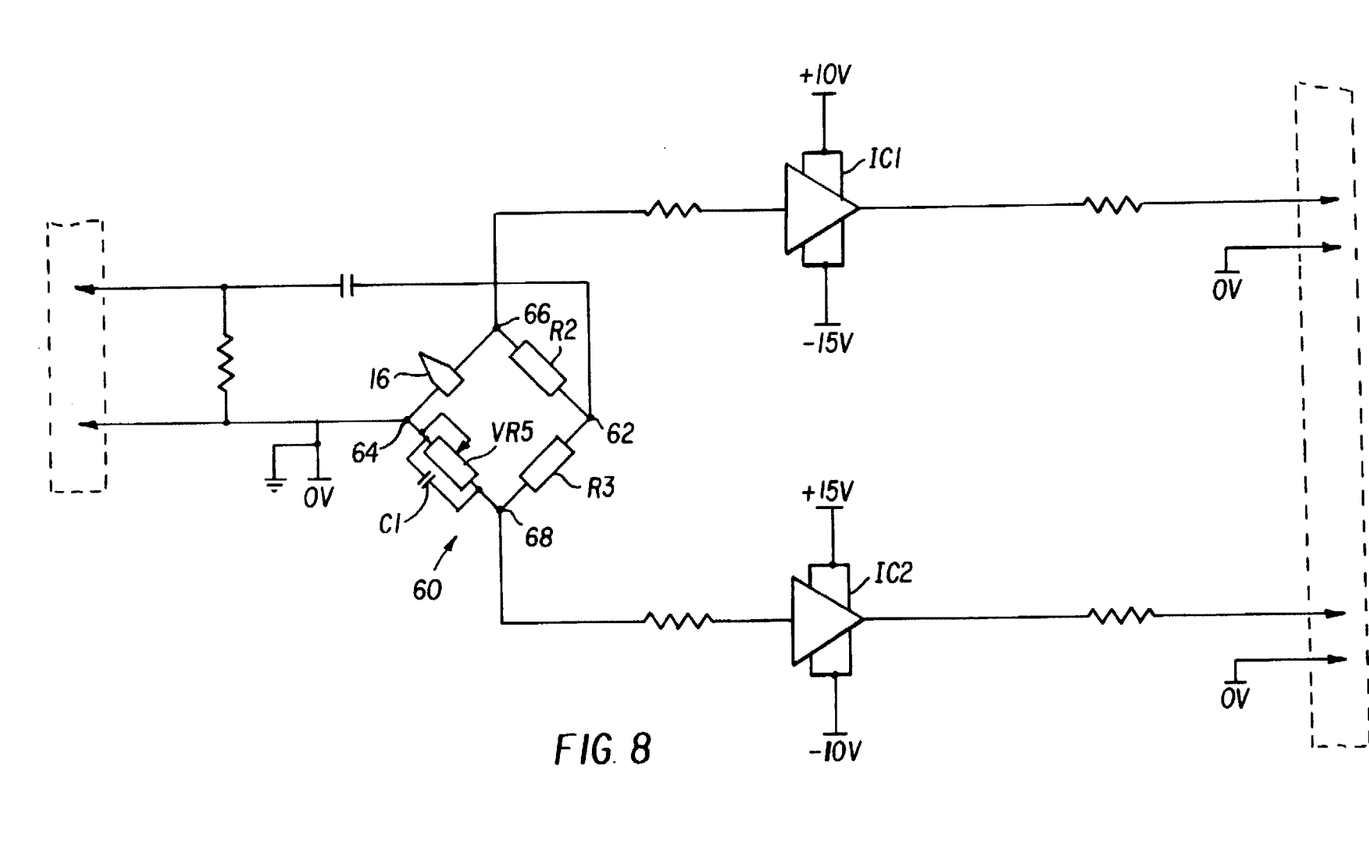
FIGS. 8, 9 and 10 are circuit diagrams.

Referring to FIG. 8, the transducer 16 is electrically connected in a bridge circuit 60 as one arm thereof, the other arms being formed by resistors $R_2$ and $R_3$ and a variable resistor VR5 (adjusted to balance the bridge). A capacitor C1 connected in parallel with resistor VR5 serves to balance out the capacitive part of the transducer, the ultrasonic a.c. signal from generator (shown in FIG. 10) being connected across the bridge between points 62 and 64 thereof (point 64 being earthed) whilst the inputs of respective line driver amplifiers IC1 and IC2 are connected to points 66 and 68 of the bridge circuit. The bridge circuitry and line driver amplifiers IC1 and IC2 are mounted in the housing 13 in close proximity to the transducer to minimize interference. The amplifiers IC1 and IC2 each have one common input/output terminal earthed, the point 64 and the earthed terminals of amplifiers IC1 and IC2 being connected to a common earth point within casing 13. Amplifiers IC1 and IC2 provide their outputs on respective coaxial cables which extend to remotely located further amplifying and processing circuitry shown in FIG. 9.

Figures 9, 9A:
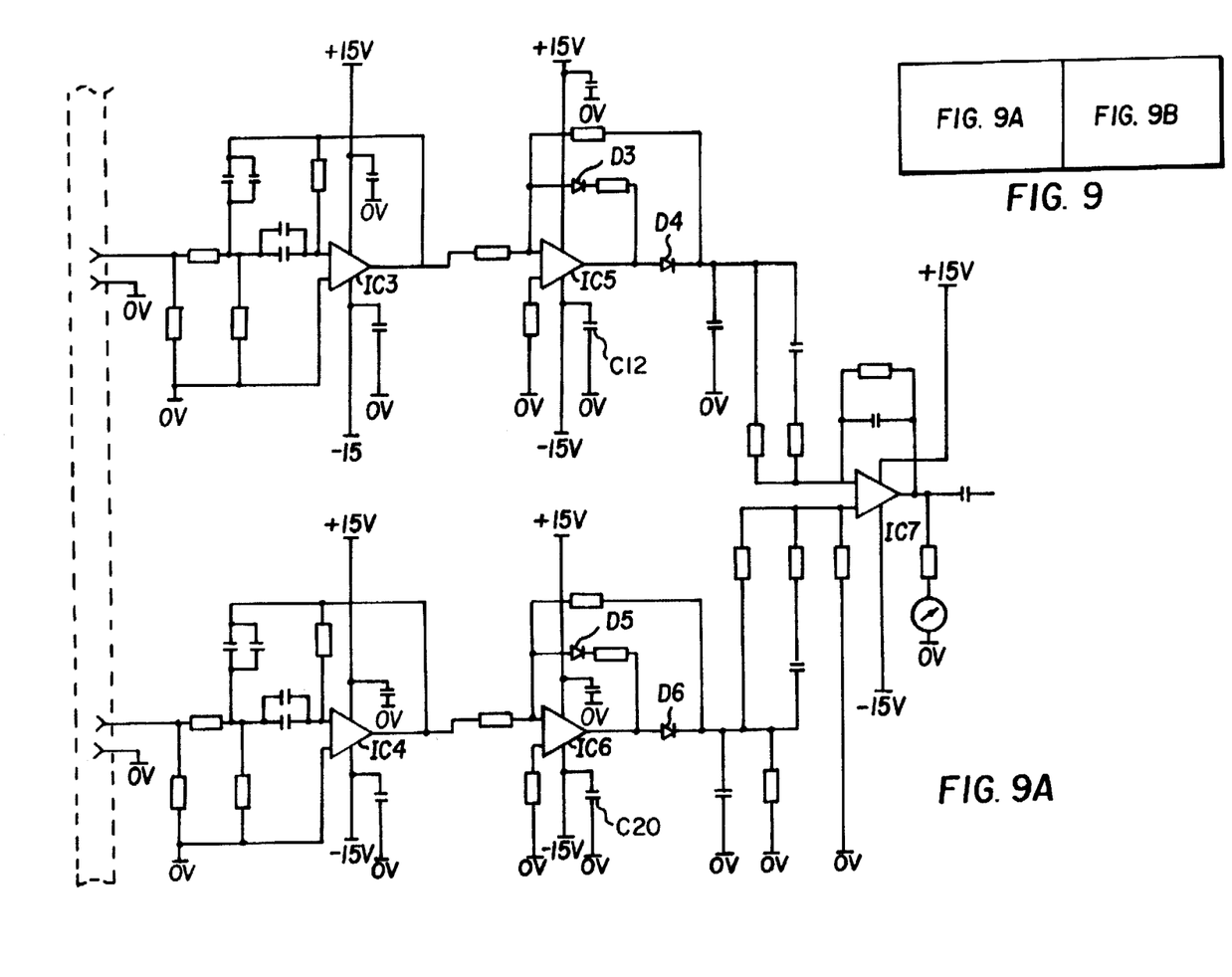
Figure 9B:
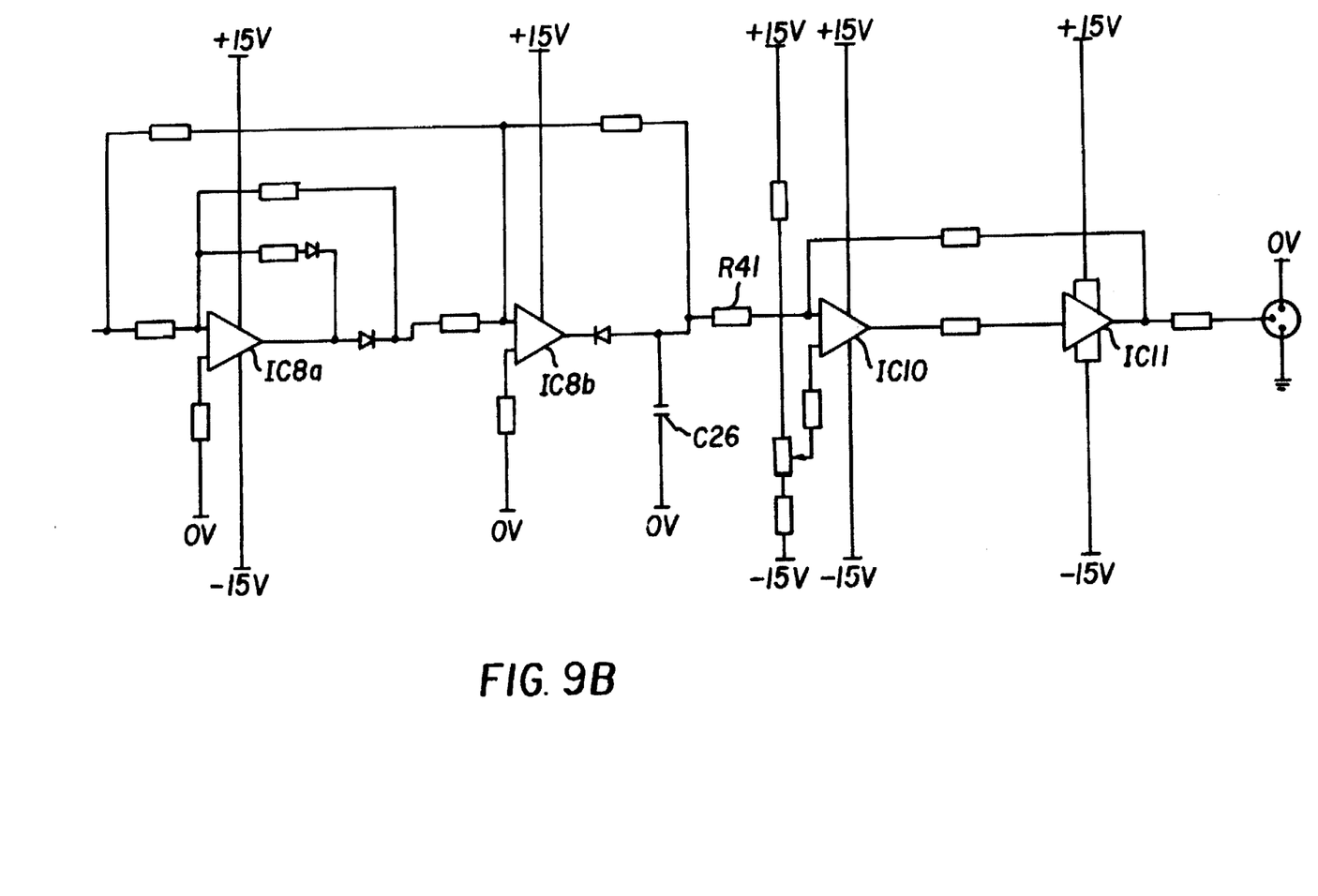
Figure 10:
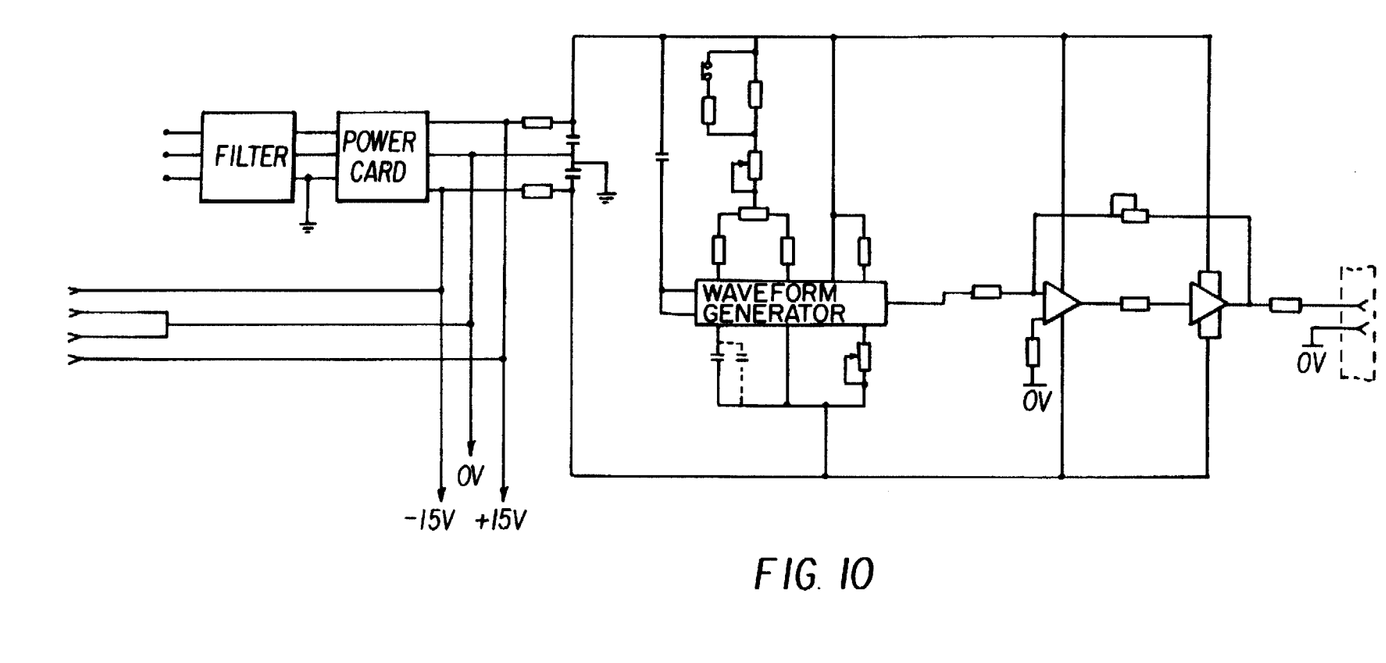

This further circuitry comprises a balanced amplifier and detector comprising two amplifier and detector channels including respectively, on the one hand operational amplifiers IC3 and IC5, and on the other hand operational amplifiers IC4 and IC6, these two channels again being balanced with respect to earth, each said channel receiving its input from a respective one of amplifiers IC1 and IC2. These channels each include an amplifier stage, incorporating the op-amp IC3 and IC4 respectively, and a detector stage, incorporating the op-amp IC5 or IC6 respectively, diodes D3, D4, D5, D6 respectively and capacitors C12 and C20 respectively.

The amplifiers incorporating op-amps IC3 and IC4 and having a gain of 2.5, are also active filters with a Q of 9. They provide rejection of unwanted harmonics of the 50 kHz working frequency which might carry some sensitivity to solids in the detector head. The 50 kHz signals from the amplifier IC1 and IC2, after amplification by the amplifier stages incorporating IC3 and IC4, are fed to the respective detector stages including diodes D3, D4 and D5, D6, which stages provide respective D.C. signals to a differential amplifier IC7 with a gain of 30. The provision of the detector stages in advance of the differential amplifier renders the circuit insensitive to any phase differences between the 50 kHz signals from line amplifiers IC1 and IC2. The output from amplifier IC7 produced by a single bubble passing through the sensor pipe takes the form of an excursion from and return to the base line representing the normal "no-bubble" signal over a period which depends upon the flow rate and corresponds to the time that the bubble is within sensing range of the transducer head, the amplitude of such excursion being dependent on bubble size. A meter permanently connected to IC7 output gives a useful indication of state of balance of the input circuits. In order to feed a low cost, slow response time chart recorder the signals from differential amplifier IC7 are A.C. coupled and rectified by a full wave rectifier including op-amps IC8a and IC8b, the full wave rectifier in conjunction with capacitor C24 forming a peak detector, the output of which is passed to the output driver stage incorporating amplifiers IC10 and IC11. The purpose of the peak detector is to make the chart recorder display independent of flow rate. C26 and R41 give the delay time constant of the peak detector.

The operating principle of the apparatus may be summarized as follows:

In operation, the transducer acts simultaneously as a radiator of ultrasound and as a receiver. In a finite medium such as the liquid contained in the sensor pipe 10, the mechanical impedance presented to the transducer by that liquid varies slightly according to whether or not bubbles are present, and this variation in mechanical impedance results in a corresponding variation in electrical impedance of the transducer, which is sensed by the balanced bridge circuit and forms the basis for bubble detection.

The voltage developed across the transducer varies in accordance with the amplitude of movement of the transducer end face and hence with the compressibility of the fluid in the sensing region of the sensor pipe 10. The bridge is balanced for bubble-free liquid so that the presence of bubbles in the sensing region of the sensor pipe 10 produces an out-of-balance bridge voltage dependent on the size and/or number of bubbles.

It is important, in this particular application, that is to say in the context of detection of bubbles in photographic emulsion, not to generate any harmonics of the ultrasonic frequency used, otherwise they may create standing waves and will result in sensitivity to solids.

In preferred embodiments of the invention, a relatively low ultrasonic frequency is used such that the corresponding wavelength in the fluid is considerably greater than any dimension relating to the cross sectional area of the sensor pipe. However, the frequency must be no lower than the resonant frequency of the minimum size of bubble to be detected. For detection of bubbles down to 60 μm in diameter, a frequency of at least 50 kHz must be used. Sensitivity to solids increases with increasing frequency.

Tests show complete insensitivity to solids at 18 kHz. Tests also show that sensitivity to individual bubbles is substantially proportional to bubble size.

The bridge circuit, in addition to affording sensitivity, serves to balance out noise and provide a balanced electrical-signal so that a balanced feeder can be used to the main part of the circuit several meters away from the transducer head.

Sensitivity in the preferred embodiments has been found to be independent of flow rate for small numbers of bubbles.

In the context of detection of bubbles in photographic emulsion it is highly desirable that no bubbles should be able to pass the detector undetected, and to this end it is desirable that the wavelength of the ultrasound used should be greater than, or at least not substantially less than the cross-sectional dimensions of the sensor pipe. However, in other fields of application it may be enough to detect a percentage of bubbles, and in such other fields a sensor pipe may be used which has a diameter many times greater than a wavelength of the ultrasound used.

Whilst, in the preferred embodiment described ultrasound is used, preferably having a frequency in the region of 50 kHz, it is conceivable that in some fields of application the minimum size of bubble which may be of interest may be so large that frequencies within the audible range may be preferred, for example frequencies down to 10 kHz or even lower, and it should be appreciated that the use of audible sound is not excluded from the scope of the invention.

The preferred embodiments of the apparatus described have the following advantages:

1) They detect all bubbles from 60 μm diameter upwards.

2) Output is proportional to bubble size for single bubbles.

3) Output is independent of flow rate over a wide range of practicable flow rates for single or small numbers of bubbles.

4) The signal produced by a cloud of bubbles is proportional to the total volume of air in the sensor pipe and to the flow rate through it.

5) Maximum variation of sensitivity to bubbles of equal size is approximately 2 to 1.

6) Minimum rejection to solid particles is approximately 30 to 1 for bubbles and solids of 1 mm diameter.

7) The apparatus is insensitive to pressure and pressure variations.

8) The apparatus is independent of temperature.

9) The apparatus is not sensitive to turbulence.

10) The bubble detector head is robust and substantially insensitive to mechanical shock and vibration.

11) The apparatus will not damage the liquid product and is non intrusive.

12) The apparatus will not trap residues.

13) No adjustment or tuning is necessary in normal operation.

I claim:

1. A bubble detector comprising a conduit for liquid to be monitored, said conduit having opposing flattened, generally parallel walls that define a gap therebetween, a transducer engaged with one of said walls and operable to apply alternating displacements to said one of said walls, at a sonic or an ultrasonic frequency, in a direction generally normal to said walls to transmit sonic or ultrasonic waves through liquid passing through the gap of said conduit, and signal generating means for generating an a.c. electrical signal at a sonic or ultrasonic frequency and for supplying said signal to said transducer to cause the latter to generate a corresponding sound or ultrasound signal, wherein the dimensions of said gap are small in relation to the wavelength of said sound or ultrasound signal.

2. A bubble detector comprising a conduit for liquid to be monitored, said conduit having opposing flattened, generally parallel walls, a tuned ultrasound-conducting and directing elements, and a transducer engaged with one of said walls and operable to apply alternating displacements to said one of said walls, at an ultrasonic frequency, in a direction generally normal to said walls to transmit ultrasonic waves through liquid passing through the conduit, wherein said transducer is an ultrasonic transducer which comprises a Langevin sandwich secured to one end of the tuned ultrasound-conducting and directing element an opposite end of which is secured to said conduit.

3. An ultrasonic bubble detector according to claim 2, further comprising means for sensing the A.C. electrical impedance of said transducer and for detecting from variations in said impedance the presence of bubbles in the liquid flowing through said conduit, said impedance sensing means comprising an a.c. balanced bridge circuit with the unknown electrical ouput impedance across said transducer being connected electrically in one arm of said bridge circuit.

4. An ultrasonic bubble detector for detecting bubbles in a liquid comprising:

an ultrasonic transducer;

a conduit for conducting the liquid;

a tuned ultrasound-conducting and directing element secured at a first end to said ultrasonic transducer, a second end of said tuned ultrasound-conducting and directing element being secured to said conduit, the presence of bubbles in the liquid causing a change in the acoustic impedance of the ultrasonic transducer which causes an analogous change in the output electrical impedance across the ultrasonic transducer;

means for supplying an a.c. electrical signal to said ultrasonic transducer to cause said transducer to generate and direct across or through said conduit ultrasonic energy; and means for sensing the a.c. output electrical impedance of said ultrasonic transducer and for detecting from variations in the a.c. output electrical impedance the presence of bubbles in the liquid flowing through said conduit.

5. A bubble detector for detecting bubbles in a flowing liquid comprising:

a sonic or ultrasonic transducer;

a conduit in which the flowing liquid is monitored, said transducer residing in a sound or ultrasound transmitting relationship transversely of said conduit;

means for generating an a.c. electrical signal at a sonic or ultrasonic frequency and for supply said a.c. electrical signal to said transducer to generate a sound or ultrasound signal, the dimensions of said conduit being small in relation to the wavelength of the sound or ultrasound signal, the presence of bubbles in the liquid flowing through the conduit causing a change in the acoustic impedance of said transducer and, consequently, in the output a.c. electrical impedance of said transducer; and means for sensing the a.c. electrical output impedance of said transducer and for detecting variations in the a.c. electrical output impedance of said transducer.

6. An ultrasonic bubble detector as recited in claim 4 wherein:

said ultrasonic transducer comprises a Langevin sandwich.

7. A bubble detector according to claim 1, wherein said means for supplying the a.c. electrical signal to the transducer is arranged to subject the liquid in the conduit to a frequency of 100 kHz or less.

8. A bubble detector according to claim 7, wherein said means for supplying the a.c. electrical signal to said transducer is arranged to subject the liquid in said conduit to a frequency of about 50 kHz.

9. A bubble detector according to claim 2, wherein said means for generating and supplying the a.c. electrical signal is arranged to subject the liquid in the conduit to a frequency of 100 kHz or less.

10. A bubble detector according to claim 9, wherein said means for generating and supplying the a.c. electrical signal is arranged to subject the liquid in said conduit to a frequency around 50 kHz.

11. A bubble detector according to claim 5, wherein said transducer is affixed to said conduit by means of silver soldering.

12. A bubble detector according to claim 5, wherein said conduit has lengths of ultrasound-absorbing material tightly fitted thereto adjacent said transducer.

13. A bubble detector according to claim 5, wherein said transducer is engaged with said conduit by means of a tuned ultrasound-conducting and directing element, whereby said transducer is demountable from said element.

14. A bubble detector according to claim 5, arranged to detect the presence of bubbles in a photographic emulsion passing through the conduit thereof.

15. An ultrasonic bubble detector according to claim 5, wherein said impedance sensing means includes an a.c. balanced bridge circuit with the electrical output impedance of said transducer being connected electrically in one arm of said bridge circuit.

16. An ultrasonic bubble detector according to claim 4, wherein said impedance sensing means includes an a.c. balanced bridge circuit with the electrical output impedance of said transducer being connected electrically in one arm of said bridge circuit.

* * * * *